(12) United States Patent
Porat

(10) Patent No.: US 6,780,195 B2
(45) Date of Patent: Aug. 24, 2004

(54) DEVICE FOR CLAMPING AND CUTTING A FLEXIBLE DEFORMABLE TUBE

(75) Inventor: Michael Porat, Tel Aviv (IL)

(73) Assignee: Starburst Technologies Limited, Tortola (VG)

( * ) Notice: Subject to any disclaimer, the term of this patent is extended or adjusted under 35 U.S.C. 154(b) by 162 days.

(21) Appl. No.: 10/141,350

(22) Filed: May 9, 2002

(65) Prior Publication Data

US 2002/0169459 A1 Nov. 14, 2002

Related U.S. Application Data

(63) Continuation-in-part of application No. PCT/IL00/00734, filed on Nov. 9, 2000.

(30) Foreign Application Priority Data

Nov. 14, 1999 (IL) ................................................ 132913

(51) Int. Cl.⁷ .......................... A61B 17/42; A61B 17/46; A61B 17/08; A61B 17/32; A61D 1/10
(52) U.S. Cl. ........................ 606/120; 606/157; 606/174; 606/183
(58) Field of Search ................................ 606/119, 120, 606/151, 157, 158, 167, 174, 181, 182, 183; 269/237, 257, 259, 264, 271, 104, 157, 161, 216, 2, 6, 13, 37, 43, 47, 86, 87.1, 89, 90, 91, 93; 30/134, 135

(56) References Cited

U.S. PATENT DOCUMENTS

| | | | |
|---|---|---|---|
| 410,375 A | * | 9/1889 | Norrell .......................... 30/135 |
| 4,733,701 A | * | 3/1988 | Loisel et al. ................ 140/93.2 |
| 5,127,915 A | * | 7/1992 | Mattson ........................ 606/120 |
| 5,423,831 A | * | 6/1995 | Nates ........................... 606/120 |
| 5,462,555 A | | 10/1995 | Bolanos et al. |
| 5,591,173 A | | 1/1997 | Schifano |
| 5,797,922 A | * | 8/1998 | Hessel et al. ................ 606/120 |
| 5,863,033 A | * | 1/1999 | Bradford ......................... 269/3 |
| 5,925,052 A | | 7/1999 | Simmons |
| 5,938,666 A | * | 8/1999 | Reynolds et al. ............ 606/120 |
| 6,227,081 B1 | * | 5/2001 | Bally et al. .................... 81/389 |
| 6,257,039 B1 | * | 7/2001 | Childress ....................... 72/211 |
| 6,311,586 B1 | * | 11/2001 | Hirse ............................. 81/99 |

FOREIGN PATENT DOCUMENTS

| | | | | |
|---|---|---|---|---|
| EP | 0121474 | | 10/1984 | |
| WO | WO 97/36715 | * | 10/1997 | ........... B25B/13/28 |
| WO | WO 97/36717 | * | 10/1997 | ........... B25B/13/28 |
| WO | 9940863 | | 8/1999 | |

* cited by examiner

Primary Examiner—Kevin Shaver
Assistant Examiner—Anuradha Ramana
(74) Attorney, Agent, or Firm—Dennison, Schultz, Dougherty & MacDonald

(57) ABSTRACT

An instrument for clamping and cutting a deformable flexible tube includes handles and jaws pivotally coupled together on opposite sides of a pivot member, a fixed cutting blade on the jaws, integrally hinged lockable V-clamps with ratcheted inner gripping surfaces mounted in the jaws with the edge of the cutting blade positioned above the ratcheted surfaces of the V-clamps, and a device to push the V-clamp axially forward in the jaws. When the handles are pressed together to an intermediate position, the jaws are closed only partially locking the arms of the V-clamps while leaving the edge of the cutting blade distanced from the center of the clamp and from the tube, and when the handles are pressed further to a cutting position, the locked V-clamp is pushed forward in the jaws simultaneously closing the jaws completely and bringing down the cutting blade.

15 Claims, 5 Drawing Sheets

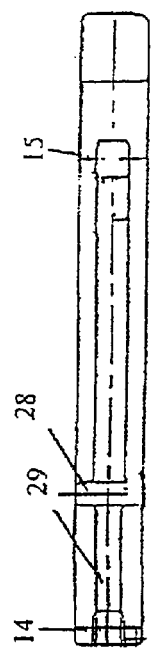
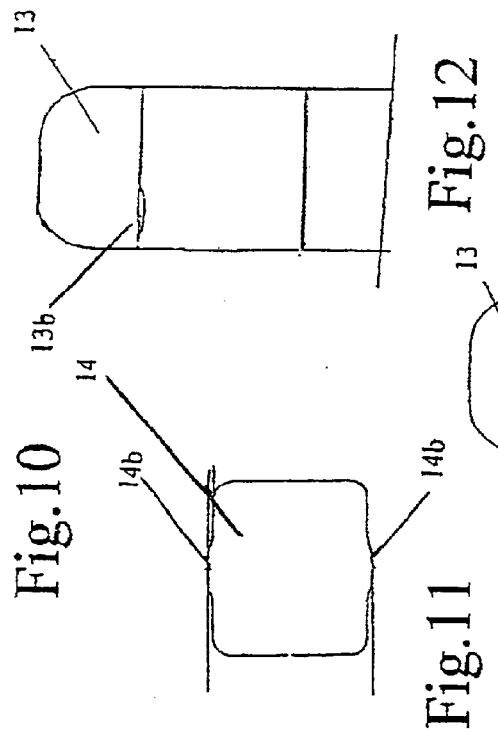
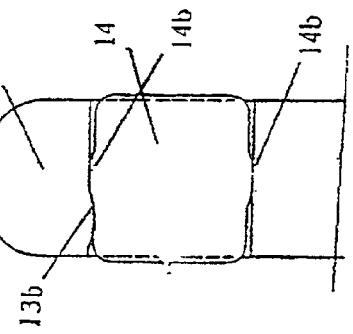
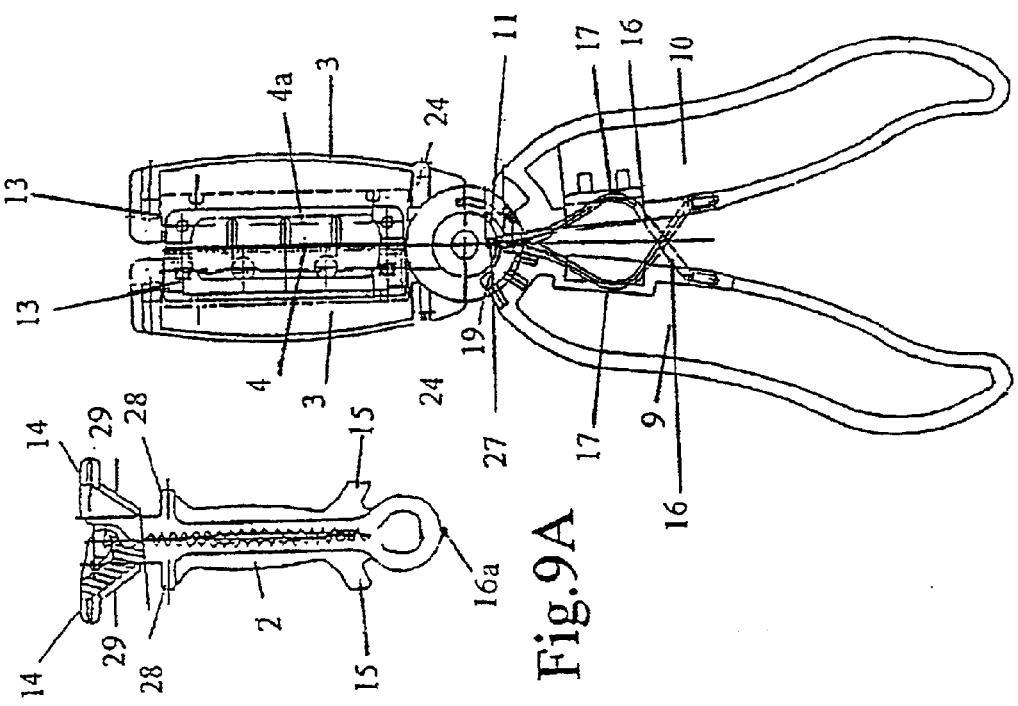

DEVICE FOR CLAMPING AND CUTTING A FLEXIBLE DEFORMABLE TUBE

This application is a continuation-in-part of PCT/IL00/00734 filed Nov. 9, 2000.

BACKGROUND OF THE INVENTION

The present invention relates to a surgical instrument for clamping and severing the umbilical cord of a newborn infant and a methods of constructing and utilizing such instrument. In particular, this invention relates to an instrument that first clamps and immediately afterwards cuts the umbilical cord all in one continuous action. The instrument can also be used to clamp and cut any artificial or natural deformable tube that is capable of being clamped and then severed, particularly tubes containing flowing fluid such as body fluid or water. Examples of such tubes are umbilical cords, infusion tubes, dialysis tubes, irrigation tubes, etc.

The umbilical cord is a flexible tube that connects the fetus to the placenta and contains two arteries and one vein that carry blood in and out between the fetus and the placenta.

A common method today for clamping the umbilical cord prior to cutting it is to use V shaped clamps. These clamps are fabricated from flexible material and comprise a pair of arms joined together at one end by an integral hinge-forming loop of substantial diameter. The free ends of the arms terminate in head portions that are normally spaced apart. The arms are movable towards each other by a compressive force. The head portions of the V clamps have means for locking the arms when pressed together thereby clamping the umbilical cord therebetween.

After an infant is born, the umbilical cord is clamped by a first V clamp as close as possible to the infant and then cut. In order to avoid blood squirting out of the open end of the cut cord another common method uses two V clamps. The second clamp is clamped about 5 centimeters towards the placenta and a pair of scissors is used to cut the cord between the clamps.

Another method is to use four V clamps, where the third clamp is placed about 10 centimeters from the second clamp and the fourth clamp is placed about 5 centimeters further towards the placenta. The umbilical cord is then cut twice, first between the first and second V clamps and then between the third and fourth clamps. This way a sausage like tube, of about 10 centimeters long, is formed containing infant's blood which is then used for testing.

The above described methods still have some disadvantages since they require precious seconds to clamp and cut the umbilical cord, seconds than may make the difference between a routine delivery or one complicated by serious lung problems.

Various devices and procedures have been developed to clamp and cut the umbilical cord.

U.S. Pat. No. 3,150,666 discloses a device for clamping one end of an umbilical cord and then applying an elastic band around the umbilical.

U.S. Pat. No. 3,166,071 discloses a device for simultaneously applying two spaced umbilical cord clamps and severing the umbilical cord there between.

U.S. Pat. No. 4,026,294 requires two actions, first to clamp and then open the scissors to move them, and then to cut.

U.S. Pat. Nos. 4,428,374 and No. 4,648,401 disclose simultaneously clamping and severing the umbilical cord. This simultaneous action is dangerous as previously explained.

U.S. Pat. Nos. 4,556,058, 4,469,346, 4,576,165 and 4,572,181 disclose devices that are not scissors shaped and their action is by means of a vertical movement which first clamps the umbilical cord and later severs it by moving a blade through the clamped cord. This procedure requires bringing the cord into the device manually with one hand and using the other hand to operate the instrument. In a scissors action, only one hand is needed and the other hand is free.

U.S. Pat. Nos. 4,716,886 and 4,938,215 do not use a scissors like instrument to clamp and sever the umbilical clamp. They use a shear pin between the two clamps that is severed by the blade as well, enabling the two clamps to separate. Such a shear pin is dangerous as it might break into smaller pieces endangering the infant.

U.S. Pat. No. 4,870,965 discloses a double upper handle, the first one to clamp the clamps and the second to eject the clamped umbilical cord from the device.

U.S. Pat. No. 5,009,657 also simultaneously clamps and severs the umbilical cord. A tab (62), formed on the central section of the clip, is used to release the clamps from the device after the cord is severed and not before the act of severing as suggested in this invention.

U.S. Pat. No. 5,127,915 discloses simultaneously clamping and severing the umbilical cord. The device disclosed therein allows release of the clamp immediately after the severance, again, not before the act of severing as invented in this invention.

U.S. Pat. Nos. 5,190,556, 5,415,665, 5,520,699 and 5,575,796 disclose instruments that are not scissors like, and their main objective is to collect the blood from the mothers end of the cord.

U.S. Pat. No. 5,462,555 also discloses an instrument that is not scissors like and that does not use handles to clamp and later sever the cord.

U.S. Pat. Nos. 5,584,840, 5,667,516 and 5,817,103 disclose instruments that are also not scissors like.

U.S. Pat. No. 5,676,672 of suggests a method to clamp and sever the umbilical cord using a tube like device, which does not resemble scissors.

U.S. Pat. No. 5,591,173 discloses a scissors like apparatus for clamping a compressible body prior to cutting it, such as an umbilical cord, which is different from the device of this invention.

The major problem with scissors-like devices is that there is always the risk that the cord will be severed before it is completely clamped and squashed. It is essential that first—the umbilical cord be safely clamped and only afterwards—that it be cut. Some instruments clamp and sever the umbilical cord simultaneously and this is very dangerous. If the clamps are not yet completely closed before the cutting action, blood will spurt out of the infant's side with all its consequences. In a worst case scenario, the umbilical cord will be cut before the clamps are completely closed and secured. In this case, the ends of the cord may slip out of the clamp leaving the severed cord open allowing blood to burst from the infant end. In the case of scissors-like devices, which have the V clamps mounted on the scissor jaws, the clamps can be completely closed, however, further movement of the handles on the other side of the pivot to completely close them is not possible. This inability to continue the movement of the handles after the clamps are securely closed prevents the clamping and severing of the cord in one continuous action.

The World Health Organization (WHO) has emphasized in it's three latest publications regarding childbirth ("Care in Normal Birth: a practical guide", 1999; and "Essential Newborn Care, Report of a Technical Working Group (Trieste, 25–29 Apr. 1994)"; and "Care of the Umbilical Cord, A review of the evidence" 1999) that only after secure clamping of the umbilical cord has been completed, the cord should be cut.

It is a preferred object of the current invention, to provide a scissors like surgical instrument that will clamp the umbilical cord and sever it-near the clamp. By exerting pressure on the handles of the instrument two operations will be performed by the jaws at the other end of the pivot. The V clamp held in the jaws will clamp the cord securely closed and only afterwards will the blades cut the cord when xerting additional pressure on the handles. As stated before, it is essential that first the umbilical cord is safely clamped and only afterwards that it will be cut.

SUMMARY OF THE INVENTION

Our invention consists of a scissors like device onto which on the blades side is attached at least one clamp in a V shape, or two clamps in a V shape, one on each side of the scissors jaws. The V shaped clamps are fabricated of semi-rigid material and comprise a pair of arms joined together at the apex of the V by an integral hinge-forming loop of substantial diameter. The free ends of the arms are normally spaced apart and terminate in head portions. The head portions of the V clamps carry means for locking the arms together in the clamping position. The arms are movable towards each other by a compressive force to clamp the umbilical between them.

At least one blade is positioned on the jaw of the scissors adjacent the clamp, so that it is above or below the plane of the inner surface of the V clamp. In a preferred embodiment of the invention, two blades are positioned one in each jaw. The blade is placed so that the sharp part of the blade is at least 0.001 mm. above or below the plane of the inner surface of the clamp.

The lateral distance of the blade, or blades, from the V clamp, can be the width of the jaws, or half of it if we use two clamps. The closer the clamp is to the blade, the shorter the stump which remains on the severed edge of the cord.

The scissors must be designed so that even when the clamps are completely closed, the two handles on the other side of the pivot, do not reach each other. The scissors must not allow the handles to reach their closed position, if the clamps are not yet closed The umbilical cord is placed between the two open jaws containing the blade or blades which are "hidden" by the V clamp or the two V clamps. When pressure is exerted on the scissors handles, the arms of the V clamps are closed and locked together with the umbilical cord squashed between them At this stage the blades on the jaws do not yet reach the cutting position as they are still beyond the middle plane of the V clamps. The handles on the other side of the scissors pivot have reached the end of their movement, with the jaws partly closed, but still have a way to go. However, they are prevented from further movement by the closed V clamps, which do not allow the jaws to come closer to each other.

At this stage, the V clamps are pushed forward axially with respect to the jaws, proportionate to their previous position. This proportionate movement is achieved by pushing the V clamps forward releasing and detaching the clamps from their initial fixed position in the jaws. The movement of the V clamps out of their grip, allows the jaws to move closer and close fully, enabling further moving of the handles towards their closed position, while simultaneously enabling the blades to sever the tube.

The movement of the V clamps out of the grip can be achieved by using a spring that is activated by pressure on the handles and results in pushing the clamps. This action will be explained in detail later. Another way to release the V clamp from their grip can be achieved by a tab near the scissors pivot, close to the arch of the V clamp base. The tab is designed so that it is not even, and when the handles move towards each other, it pushes the base of the V clamps forward.

Release of the clamps from the cradle can also be achieved by use of a wedge, or wedges, on the jaws. The wedge will push the V clamps out of their grip by entering between the V clamp and the jaws pushing them far from each other, thus releasing them from the grip.

In the above-described invention, the attendant will place the umbilical cord between the two V clamps in the jaws and close the handles in a continuous scissoring moving action until the cord is severed. The movement of the handles will first grip, clamp and squash the cord, then move the clamp forward out of the cradle closing the jaws completely, and sever the cord by means of the blade or blades. The attendant, while moving the handles will perform one continuous action, whilst on the jaws end, three consecutive actions have been performed: clamping the cord, moving the clamp forward to close the jaws completely and cutting the cord.

The fastest current procedure (not using our invention), will require 6–7 seconds for cord severing whilst our novel procedure will take 1 second. This will provide the attendant with an opportunity to suction the infant's air passage virtually before the infant's first breath or at most its second breath, thus preventing material from reaching far into bronchi, by means of direct tracheal suctioning by the attendant.

As stated before, the basic idea in our invention is to use a scissors-like device to perform clamping of the umbilical cord, using regular and commonly used V shaped clamps in the art of clamping the umbilical cord. In the same action of movement of the handles at the other side of the pivot—after the V clamps are securely closed and the posterior handles have reached their final position for clamping, the clamps are detached from their first position by moving them forward. The first position does not enable the blades to sever the cord, only the detachment and advancement of the V clamps from their position permits the blades to proceed with their severing action and cut the cord.

The above-described phenomena can be achieved by adding to the device, a push spring which will detach the V clamps after they are securely closed.

Another way to achieve the detachment is by means of a protrusion-tab placed close to the V clamps that detach the V clamps permitting the continuation movement of the blades to cut the cord. The spring or the protrusion can be placed near the base of the V shaped clamps, which will push the V clamps forward.

Another way is to use a wedge or wedges on the bases of the jaws that hold the V clamps near the blades; the wedge, when the V clamps are closed, will move the V clamps to the side. By moving to the side, the V clamp is detached from its grip, thus permitting passage of the blades and for cutting the umbilical cord clamp.

Another possibility is to use the spring or protrusion-tab system with the wedge on the scissors jaw. This combination will secure the cutting of the umbilical cord, only after the V clamps are securely closed, and the wedges, pushing the clamp to the side, will facilitate the release of the clamps from the device.

BRIEF DESCRIPTION OF THE DRAWINGS

The invention will be understood more clearly with reference to the drawings in which;

FIG. 9 is a side elevation view of the instrument of FIG. 8. in a fully closed position with the blades in a cutting orientation.

FIG. 9A shows the closed V clamp of FIG. 8A as it is held in the jaws of the instrument in a pushed forward position.

FIG. 10 is a top view of the V clamp of FIG. 7.

FIG. 11 is a top view of the protrusion in the form of a rounded mound at the front of the V clamp of the other preferred design using the "push spring".

FIG. 12 is a sectional top view of the protrusion with the flat base on the front upper part of the jaws of the other preferred design using the "push spring".

FIG. 13 is a sectional top view of the protrusion with the flat base on the front upper part of the jaws including the rounded mound at the front of the V clamp in the locked position, of the other preferred design using the "push spring".

DETAILED DESCRIPTION OF THE INVENTION

Figure 1:
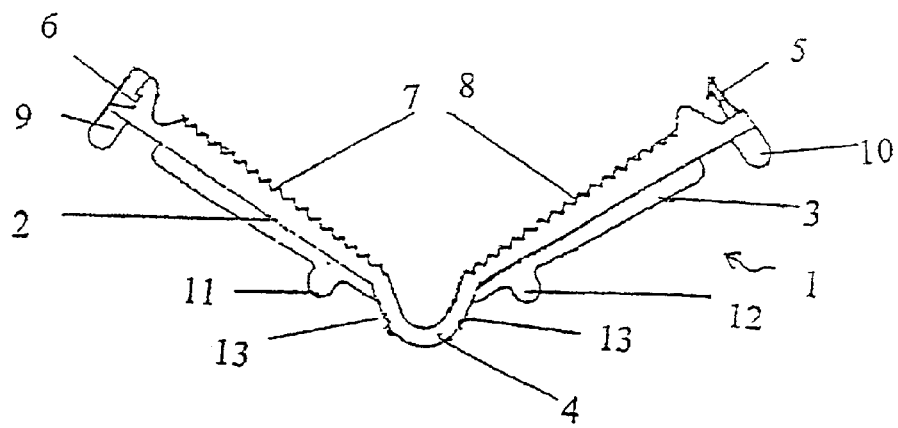
FIG. 1 is a side elevation view of an umbilical cord surgical V clamp in its open position.

FIG. 1 shows a V clamp for use in the present invention. The clamp 1 comprises clamping arms 2 and 3 hinged together by an arcuate hinge section 4. The terminal ends of the arms 2 and 3 comprise cooperating male and female locking elements 5 and 6 respectively. These elements 5 and 6 can be latch and abutment means, tongue and slot or any other cooperating locking means. The inner surface of the arms 2 and 3 are ratcheted with mating teeth 7 and 8 in order to grip the umbilical cord tightly. Near the terminal end of the back side of the clamp arms 2 and 3 there are protrusions 9 and 10 respectively, and near the hinge section 4 there are protrusions 11 and 12. These protrusions are to secure the clamp 1 in the surgical instrument 20 as will be detailed further on. Similarly, small notches 13 are preferably made on the arcuate hinge section 4 at the base of the V clamp 1. The V clamp 1 is molded from a semi-rigid plastic so that it is somewhat flexible yet unbreakable, such as from acetal or polyamide. The clamps 1 are molded with their arms 2 and 3 widely spread apart thereby providing springy resistance when squeezed together. To insert the clamps into the jaws of the instrument 20 (see FIG. 2.) the arms 2 and 3 are squeezed together slightly and the compressed clamp inserted between the jaws 26 and 27, thereby securing the clamp 1 in the jaws 26 and 27.

Figure 2:
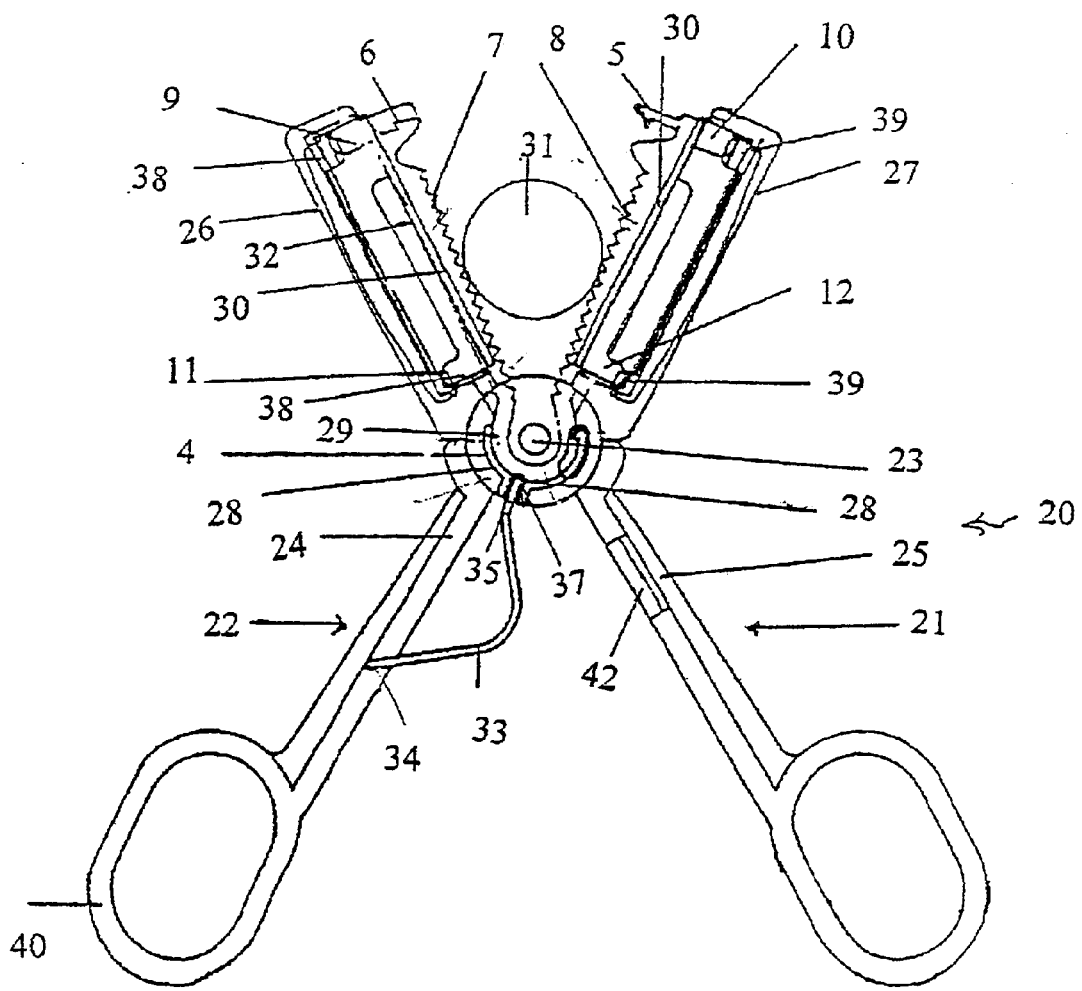
FIG. 2 is a side elevation view of a surgical instrument in the open position for clamping and severing the umbilical cord, in accordance with the present invention.
Figure 3:
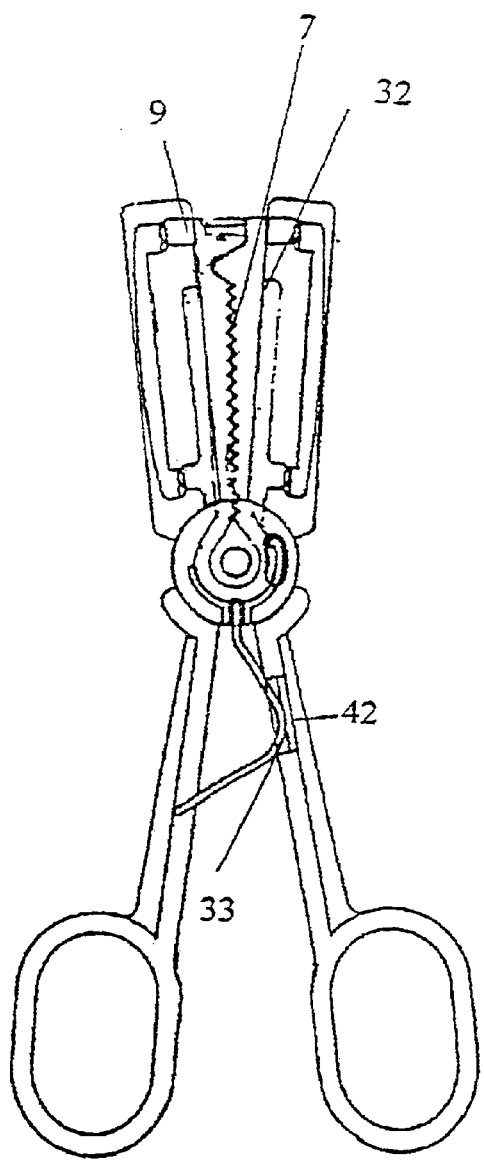
FIG. 3 is a side elevation view of the surgical instrument of FIG. 1 in a closed position in which the umbilical cord V clamps are completely closed and the cutting blades have not yet severed the umbilical cord.
Figure 4:
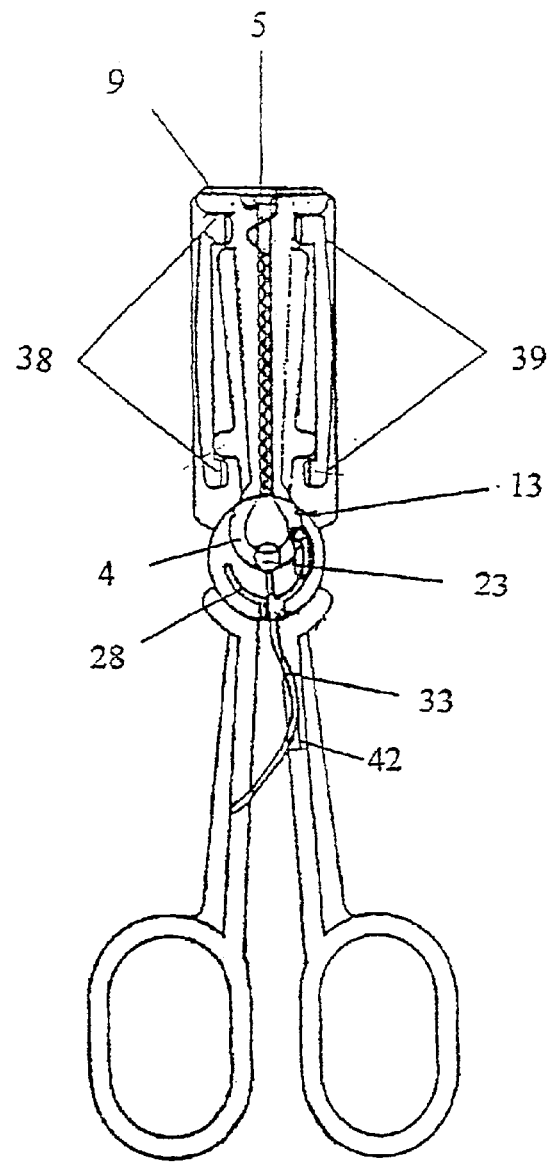
FIG. 4 is a side elevation view of the surgical instrument of FIG. 1 in a cutting position after the V clamps have been pushed forward and the blades have severed the umbilical cord.

Referring now to FIGS. 2 to 4, there is shown a surgical scissor-like instrument 20 comprising first 21 and second 22 scissor members pivotally coupled together by a pivot member 23 to selectively move between a first open position (FIG. 2), an intermediate closed position (FIG. 3) and a cutting position (FIG. 4). The instrument 20 comprises handles 24 and 25 on one side of the pivot member 23, and jaw elements 26 and 27 on the other side of the pivot member 23. The jaw elements 26 and 27 face each other, and at the base near the pivot member 23 of a scissors member, there is provided an arcuate flanged cradle support 28 for receiving the arcuate hinge section 4 of the V clamp 1. The cradle support 28 has protrusions 29 that fit into the notches 13 of the arcuate hinge section 4, and the jaw elements 26 and 27 have recesses 38 and 39 to receive the protrusions 9, 10, 11 and 12 of the clamp 1 to help secure clamp 1 in the jaws 26 and 27. A sharp cutting blade element 30 is mounted on one of the jaw elements 26 and 27 adjacent the V clamp 1 for cutting the umbilical cord 31 by squeezing together the handles 24 and 25. The cutting edge 32 of the blade element 30 is positioned in the jaw 26 or 27 (or in both if the jaws are designed to hold four clamps) above the ratcheted surface 7 of the clamp arm 2 or 3 so that even when the instrument handles 24 and 25 are squeezed to close the clamp 1 over the umbilical cord 31 the cutting edge 32 will not sever the cord 31. At this point the handles 24 and 25 still have enough space between them to squeeze them even further together, since the jaws 26 and 27 are not completely closed. A spring arm 33 is attached at one end 34 to the handle 24, the other end 35 entering the space 37 in the base 36 of the cradle support 28 on the pivot member 23. The spring 33 has an approximate angle of 90° which keeps the handles 24 and 25 wide apart and maintains the angle 37 between the clamp arms 2 and 3 in a wide open position until the handles 24 and 25 are squeezed together and the spring is pressed against the stop 42. The purpose of the spring 33 is to push the clamp 1 forward when the handles 24 and 25 are completely squeezed together. The spring 33 thus extends through the space 37 into the cradle support 28 forcing the arcuate hinge section out of the cradle 28 enabling the jaws 26 and 27 to close and the handles 24 and 25 to meet, thereby lowering the cutting edge 32 past the plane of the ratcheted surface 7 to cut the umbilical cord 31. In the present embodiment, the terminal ends of the handles 24 and 25 of the scissor members 21 and 22 form loops 40 like conventional scissors. However other types of handles can also be used. In a preferred embodiment, the surgical element has jaws that accommodate two V clamps with a cutting blade between them.

In another embodiment of the invention, the arcuate base 36 can be integrally formed with the spring arm 33. In this case, the end of the spring arm 33 and the arcuate base 36 will be disconnected from the round surface around the pivot member 23.

The springiness of the V clamp 1 is assured by the protrusions 9, 10, 11 and 12 held in recesses 38 and 39 on each side of the two jaws 26 and 27, and by the protrusions 29 of the arcuate cradle support 28 fitted into the notches 13 on the arcuate hinge element 4 keep the V clamp firmly in place.

A tooth serrated surface can be placed near the gripping part, facing inwards to fit on the opposite handles. When the device closes, the teeth fit into each other, and prevent easy opening of the scissors-like device. These serrated surfaces are not necessary to operate the device, but they provide a safety measure to avoid injury from the sharp blades after use.

METHOD OF USE OF THE PREFERRED DEVICE

We shall now describe the operation of an inventive instrument with two V clamps. The same description will apply to a device with one V clamp facing the infant.

Immediately after the birth, the umbilical cord 31 is placed between the two V clamps 1. Pressure is applied as in a cutting motion of regular scissors. The pressure closes the V clamps 1 to their final "close" position. The device is designed so, that in this position, as shown in FIG. 3, the spring 33, has not yet reached the base of the housing.

As a result of continued pressure on the gripping parts, the handles 24 and 25 become arched (not shown) and the spring 33 is forced to extend into the arcuate cradle 28 as illustrated in FIG. 4. If the arched cradle support 28 is an integral part of the spring 33, the arcuate base 36 will push the closed V clamp forward. The spring 33 pushes forward the already closed V clamp 1 with the umbilical cord (not shown) gripped therein, and releases the protrusions of the clamps from the recesses in the jaws. The distance the V clamps 1 are pushed forward is sufficient to move the protrusions 9, 10, 11 and 12 out of the respective recesses of the jaws in FIG. 4. The release of the protrusions enables the jaws to become closer to each other and close completely as illustrated in in FIG. 4, with the blades having already severed the umbilical cord.

At the end of the procedure, the V clamps 1 are left closed in the hands of the attendant, one V clamp 1 is left on the severed umbilical cord facing the infant, and the other one is left facing the placenta.

The attendant who severs the cord performs only oneaction, pressing the handles, thereby clamping and cutting the umbilical cord. He does not have to stop the motion of the handles from the beginning to the end.

The controlled pressure exerted on the handles is enough to first clamp and then sever the cord. No unusual force is required compared with the force needed to close the commonly used V clamp. The umbilical cord is placed at a distance from the pivot which is less than half of the distance from the beginning of the loops to the pivot. It is a rule of physics that the power needed to clamp the V clamps is equal to the multiplication of the distance between the pivot and the loops. If the distance is doubled then the force needed is reduced to half. Therefore, if the distance from the pivot is longer, the less power is needed, in the same ratio. If the distance is more than double, the power needed to close two V clamps will be less than needed to close one V clamp from the front of the V opening.

Figure 6:
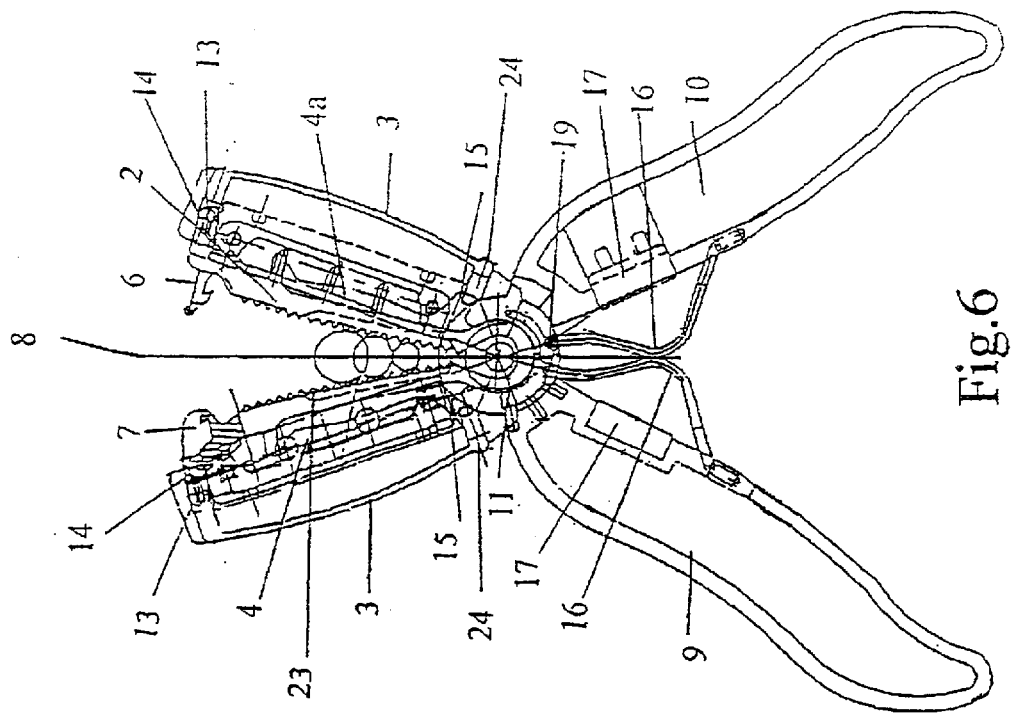
FIG. 6 is a side elevation view of still another embodiment of a surgical instrument of the invention.
Figure 5:
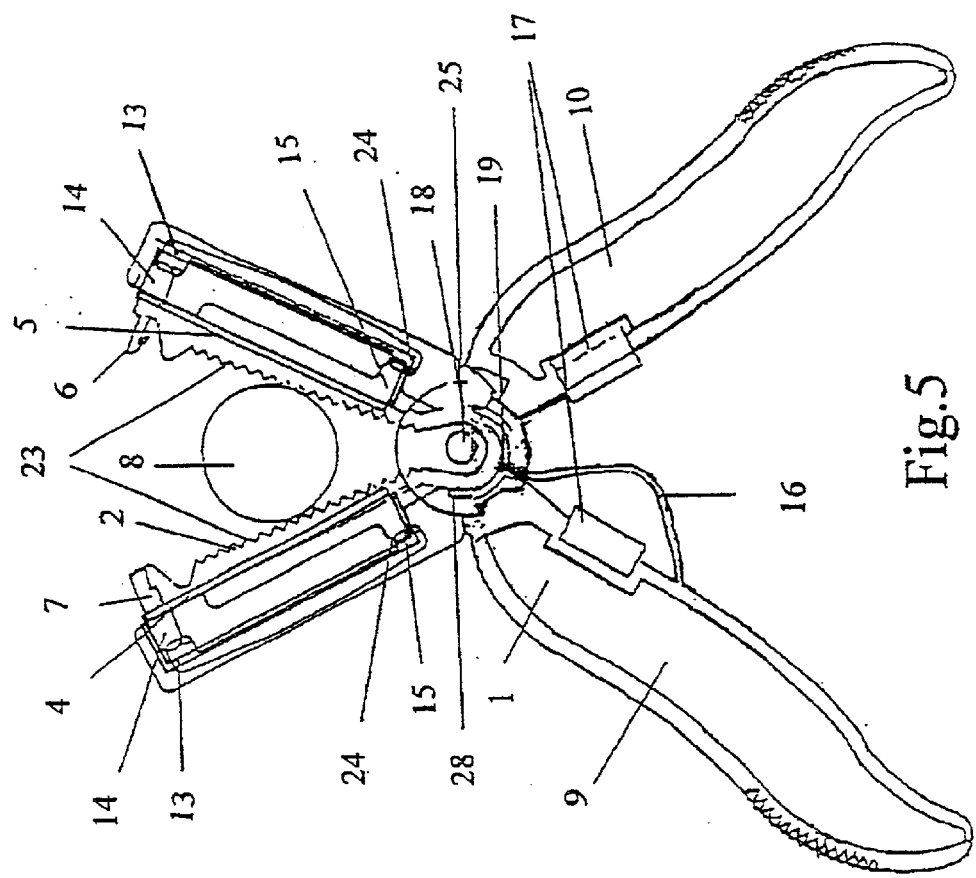
FIG. 5 is a side elevation view of another embodiment of a surgical instrument of the invention.
Figure 8A:
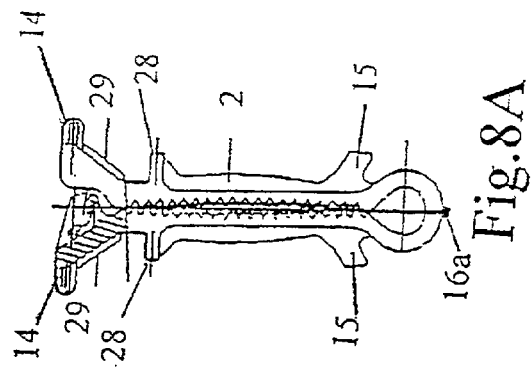
FIG. 8A shows the V clamp of FIG. 7 in a closed position when held in the jaws of the instrument of FIG. 8.
Figure 8:
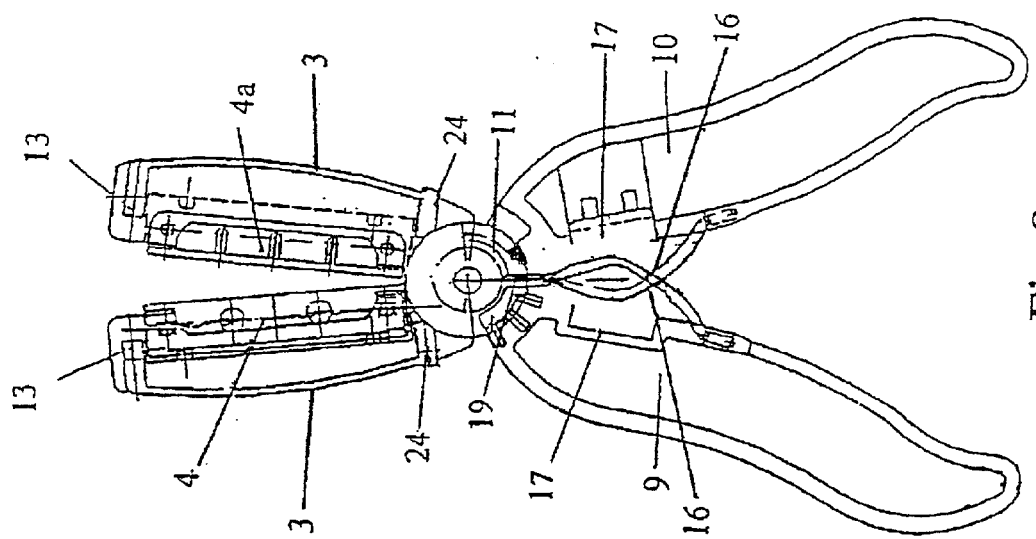
FIG. 8 is a side elevation view of yet another embodiment of a surgical instrument in accordance with this invention for use with clamps shown in FIG. 7 shown in partially closed position.
Figure 7:
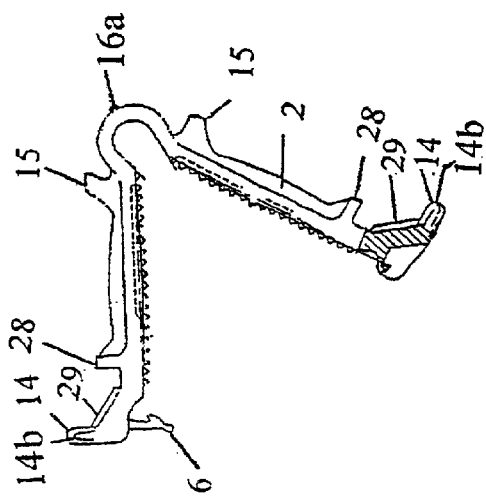
FIG. 7 is a side elevation view of another preferred surgical V clamp for clamping an umbilical cord in accordance with the invention.

Referring now to another preferred design of the surgical instrument of the invention using a "push spring" preferred system there are shown in FIGS. 6,8 and 9 two identical handles (9) and (10) manufactured from reinforced polyamide. On the front of the device we see the V shape clamp (FIGS. 6–9) (2). (In some diagrams, (FIGS. 8–9) because it is difficult to distinguish between the clamp and the other parts, we have illustrated the clamp on the side, parallel to its original position). The V clamps are seated between the two jaws held by the pressure they create due to their flexibility (FIG. 6). The V clamps, (2 in FIG. 7) are made of elastic Polyamide or Acetal resin. At the top of the V clamps, male+female locks (FIGS. 6–7) (6+7) are so positioned at an angle to allow the flexible male lock (6) to enter the female lock (7) which is designed to match the male lock (6) and once entered and matched will keep the clamps in a closed position. The V clamps are molded in a larger open V shape, wider than the maximum opening potential of the jaws. The V shaped clamps are pressed and inserted between the two jaws. The flexible reflex of the V shaped clamps will hold the scissors in the open position.

On the outer ends of the V shaped clamps, on each side there is a protrusion in the form of a rounded mound (FIGS. 6–10&12) (14). Near the bottom of each V clamp, on the outer surface, another protrusion in the form of a rounded end "L" shaped mound (FIGS. 6–9) (15) is placed, which protrudes backwards to the outer lower surface of the V clamps compared to the protrusion (14) on the upper part. On the upper part of the jaws, facing inwards, a protrusion with a flat base (FIGS. 6&8–9) (13) is placed opposite the protrusion (14) of the V clamp. On the lower inner side, facing inwards, a smaller protrusion (FIGS. 6&8–9) (24) is placed opposite the lower protrusion (15) of the V clamp. The outer jaws are designed to keep the V clamps in a compressed position without falling out, and with no ability to slide sideways, out of the gripping position, by a 90° angle wall on each of the protrusions (13) and (24). They will hold the clamps in position unless they are pushed forwards. The upper part of the protrusion (15) does not touch the inner higher surface of the protrusion (FIG. 6) (24) leaving a margin. (The reason for this will be explained later).

The protrusion (FIGS. 6–13) (14) is relatively less wide than the inner size of the grip (FIGS. 6&8–9&11–12) (13). On the protrusion (FIGS. 7–13) (14) there is a longitudinal protrusion on each side (FIGS. 7&10&12) (14b), so that the entire width of the protrusion (FIG. 10) (14) at this place is the same width as the inner size of the grip (FIGS. 6&8–9&11–12) (13) or even wider. The protrusion (14) on the clamp can slide with slight friction inside the cavity touching the walls of the grip (13). In the inner part of the grip (FIG. 16) (13), on the outer sidewall there is a frontal longitudinal protrusion (13b), which prevents the sliding of the protrusion (FIG. 12) (14) out of the grip (13). The sliding of the protrusion (14) over the protrusion (13b) can only occur by force applied from the back of the V clamp. This is the reason that prevents the clamps from being pushed out if they are not sealed.

Towards the back of the protrusion (14) there is a monorail (FIGS. 7&13) (29) that inclines and is less wide than the inner size of the grip (FIGS. 6&8–9&11–12) (13). This inclined planed monorail ends before the block brake (FIGS. 7&13) (28) at least at the same length of the grip (FIGS. 6&8–9&11–12) (13).

A sharp cutting blade, as in a single edge razor, (FIGS. 6&8–9) (4) is placed in one jaw in a position that the sharp cutting edge is posterior to the serrated surface of the inner part (FIG. 6) (23) of the V clamp. An aerial view of the inner part of the jaws, show the blade situated near the V clamp. On the opposite jaw, opposite the blade, there is an anvil (FIGS. 6&8–9) (4a).

On the handle of the scissors-like device, there is a spring arm (FIGS. 6&8–9) (16). The spring is designed at an approximate 90° angle, starting from the handle to which it is affixed. The end of the spring is at an angle of about 120°, entering into the base (FIGS. 6&8–9) (19). On the opposite handle, opposite the 90° angle of the spring, we find a housing (FIGS. 6&8–9) (17), into which the 90° angle matches. When the handles are closed, the spring enters the housing (17) and the more the handles come closer to each other, the housing straightens the spring, so that the end of the spring penetrates further into the base of the arched base (11) (FIG. 9) (19).

Around the pivot (FIGS. 6&8–9) (25) of the scissors-like device, we find an arched base (FIGS. 6&8–9) (11) with a small indentation (19) at its base into which the end of the spring arm fits. The arched base is placed around the lower part of the circle around the pivot (25). The entire arched base is shaped to match the base of the V shaped clamps previously described.

On the center of the base of the V clamp, there is a longitudinal protrusion (FIGS. 7–9) (16a). When the V clamp is placed in the jaws, it will always be above the housing (19). (This protrusion will avoid the tendency of the spring (16) to bend upwards as was observed during preliminary tests.)

All the down mentioned positions keep the V clamp firmly in place. The springiness of the V clamp on the protrusions (14) and (15) towards the 4 flat base protrusions (13) on each side of the two jaws. The arched base (19), and the 8 90° angle walls on each of the protrusions (13) and (24) that prevents slippage to the sides, and the protrusions 13b and 14b that prevent the free slippage forward.

Following is a method of use of the other preferred design using the "push spring" preferred system:

Immediately after the birth, the umbilical cord (FIG. 6) (8) is placed between the two V clamps (2). Pressure is applied on the handles as in a cutting motion of regular scissors. The pressure reaching the force of less than 4 Kg (depends on the size of the umbilical cord and its stiffness), closes the V clamps to their final "close" position (Position of FIG. 8). The device is designed so, that in this position, as shown in FIG. 8, the spring 16, is still far from the position to reach the base of the housing (17).

As a result of continued pressure on the gripping parts, the handles (9) and (10) start to become arched (not shown). The force reached bring the bottom of the spring (16) to reach the opposite housing (FIG. 8) (17) and later it will twist between the two angles, with no other ability, but to protrude into the arch base (19), as illustrated in FIG. 9, position (27). Prior to the next stage, which is the release of the clamps from their gripped housing, a lot of energy is gathered around the pivot towards the rear handles due to the fact that the elastic handles continue their movement and the front part cannot concurrently close. All this energy will be released at once, into a firm closure of the jaws, when the clamps will be removed from their gripped position. The spring pushes forward the already closed V clamp (2) with the cord (not shown) gripped in between, over-powering the resistance of the inner protrusion 13b of the grip 13, and releases the clamps from the protrusions. The distance the V clamps are pushed in a forward position by the spring is sufficient to move the protrusions (14) and (15) out of the opposite protrusions (13) and (24) of the jaws. The protrusion (13) on the scissors jaws slips down along the monorail (29) on the V clamps till they reach the brake (28) and stop. During this rapid procedure, the gripped umbilical cord moves forward over the blade while the jaws are closed until the blade penetrates into the anvil severing on its way the gripped umbilical cord. The monorail (29) ends before the brake (28) leaving enough space for the grip (13) to slide to the sides. The umbilical cord is severed so that the two clamps do not make contact, the two sealed V clamps can leave the jaws without releasing the pressure on the handles and without opening them. At the end of the procedure, one V clamp is left on the severed umbilical cord facing the infant, and the other one is left facing the placenta. The two jaws of the device are kept closed with the blade attached to the anvil.

As there is a distance between the two V clamps in the device, the blood caught between the two jaws is under pressure and during the cut it will spurt between the jaw and the sealed clamp. In order to avoid the spurt of blood towards the attendant, there is a shield (FIGS. 6&8–9) (3) that lines the protrusions (13) and (24). This shield covers the entire line of visibility at any point between the blade and the face of the attendant.

The margin that is left between the protrusion (FIG. 6) (15) and its housing (24)) is required in cases where the umbilical cord is thick and bends when squeezed between the rear part of the closed V clamps. By allowing this distance, while closing the clamps, no force will be split to squeeze the umbilical cord between the force applied on the protrusion (14) and protrusion (15) by the handles (9) and (10). In this movement, the device performs the same action as the digital closing action performed by the attendant on the commonly used V clamp. The commonly used V clamp is designed so that the action of sealing the male and female locks (6) and (7) will bend the clamp and seal the umbilical cord.

The movement of the handles and the pressure exerted on them is enough to clamp and sever the cord. No extended force is required compared with the force needed to close the commonly used V clamp, as the cord is placed at a distance from the pivot which is less than the distance from the beginning of the loops to the pivot. It is a physics rule that the power needed to clamp the V clamps is equal to the multiplication of the distance between the pivot and the loops. If the distance ratio is 1.5 then the force needed is reduced to ⅔. The force applied by the palm of the hand is far greater than the force that can be applied by the fingers. Therefore, the scissors were designed in the form of a pliers handle, rather than a loop scissors art. Therefore, by reducing the power needed to seal the clamps to ⅔, and by designing the scissors in a pliers design, less strength is required to seal both clamps simultaneously than the strength required to seal one clamp with the fingers. Later, the palm can easily generate the force needed to perform the entire process.

What is claimed is:

1. A surgical instrument for clamping and cutting an umbilical cord by selectively moving between a first open position, an intermediate partly closed position and a cutting position comprising:

scissors members comprising handles and jaws pivotally coupled together on opposite sides of a pivot member, said jaws comprising a cutting blade and means for releasably holding an integrally hinged V clamp, a V clamp comprising two spread apart arms with ratcheted inner gripping surfaces connected by an arcuate hinge section, means for locking the arms together and means for releasably securing the clamp in the jaws, characterized in that a cradle support is provided between handle and jaw near the pivot member for receiving the arcuate hinge section of the clamp, means are provided on the scissors members to push the V clamp axially forward in the jaws, and the edge of the cutting blade is positioned in the jaw above the ratcheted surface of a clamp arm, whereby, when the handles are pressed together from a first open position to an intermediate position, the jaws are closed partially, locking the arms of the V clamp while leaving the edge of the cutting blade distanced from the center of the clamp without reaching a position of cutting the cord, and whereby, when the handles are pressed further to a cutting position, the locked V clamp is pushed forward of the cradle support enabling the jaws to close completely and bring down the cutting blade to sever an umbilical cord held in the locked arms of the clamp.

2. An instrument as in claim 1, wherein the push means is a spring.

3. An instrument as in claim 2, wherein the spring is curved having an approximate angle of 90°.

4. An instrument as in claim 1, wherein the base of the cradle support has a space through which the free end of a spring can extend.

5. An instrument as in claim 1, wherein a cutting blade is mounted on one jaw and an anvil on the other jaw for receiving the cutting edge of the cutting blade.

6. An instrument as in claim 1, wherein the jaws hold two V clamps with a cutting blade between the clamps.

7. An instrument as in claim 1, wherein the jaws hold two V clamps and two cutting blades are mounted between them on opposite jaws with the cutting edges facing each other.

8. An instrument as in claim 1, wherein the V clamp has spread apart arms connected by an integral hinge forming a loop of substantial diameter and is manufactured from flexible material with the arms moveable towards each other by a compressive force.

9. An instrument as in claim 1, wherein the means to push the V clamp is a curved spring with one end of the spring affixed to a handle and the other free end extending through a space in the flanged cradle support, and the other handle has a stop opposite the curvature of the spring, wherein when the handles are pressed together pressure is applied to the spring at its curvature further extending the free end of the spring which pushes the clamp forward.

10. An instrument as in claim 1, provided with shields to prevent the spurting of blood towards the face of the user.

11. An instrument for clamping and cutting an artificial or natural deformable tube capable of being clamped and severed by selectively moving between a first open position, an intermediate partly closed position and a cutting position comprising:

scissors members comprising handles and jaws pivotally coupled together on opposite sides of a pivot member, said jaws comprising a cutting blade and means for releasably holding an integrally hinged V clamp, and a V clamp comprising two spread apart arms with inner gripping surfaces connected by an arcuate hinge section, means for locking the arms together and means for releasably securing the clamp in the jaws, characterized in that a cradle support is provided between handle and jaw near the pivot member for receiving the arcuate hinge section of the clamp, means are provided on the scissors members to push the V clamp axially forward of the cradle support in the jaws, and the edge of the cutting blade is positioned in the jaw above the ratcheted surface of a clamp arm, whereby, when the handles are pressed together from a first open position to an intermediate position, the jaws are closed only partially locking the arms of the V clamp while leaving the edge of the cutting blade distanced from the center of the clamp without reaching a position of cutting the cord, and whereby, when the handles are pressed further to a cutting position, the locked V clamp is pushed forward of the cradle support enabling the jaws to close completely and bring down the cutting blade to sever a deformable tube held in the locked arms of the clamp.

12. A scissors member for pivotally connecting to another scissors member to form a surgical instrument for engaging a V clamp for clamping and cutting an umbilical cord, comprising:

a handle with a double jaw section and a pivot member between the jaw and handle, a cutting blade mounted in the middle of the double jaw section, a flanged arcuate cradle support having a space in the flange provided between the handle and double jaw near the pivot member, a curved leaf spring having one end affixed to one side of the handle and the other free end extending through the space in the flange of the cradle for engaging a V clamp, and a stop affixed to the other side of the handle opposite the curve of the spring.

13. A method of clamping and cutting a deformable tube capable of being clamped and then severed, comprising:

a) providing an instrument comprising:

scissors members comprising handles and jaws pivotally coupled together on opposite sides of a pivot member, said jaws comprising a cutting blade and means for releasably holding an integrally hinged V clamp, a V clamp comprising two spread apart arms with ratcheted inner gripping surfaces connected by an arcuate hinge section mounted between the jaws, means for locking the arms together and means for releasably securing the clamp in the jaws, means on the scissors members to push the V clamp axially forward in the jaw without fully closing the jaw, b) inserting a deformable tube between the ratcheted surfaces of the spread apart arms of the V-clamp when the device is in a first open position, c) pressing the handles to an intermediate position where the jaws are only partially closed thereby locking the arms of the clamp and squeezing the tube tightly therebetween leaving the cutting edge of the cutting blade distanced from the inner surfaces of the locked arms, and from the tube, and d) further pressing the handles to push the locked V-clamp forward in the jaws, simultaneously closing the jaws completely and bringing down the cutting blade to sever the tube held in the clamp.

14. A method as in claim 13, wherein the deformable tube is an umbilical cord.

15. A scissors member for pivotally connecting to another scissors member to form a surgical instrument for engaging a V clamp for clamping and cutting an umbilical cord, comprising:

a handle with a double jaw section and a pivot member between the jaw and handle, an anvil mounted in the middle of the double jaw section, a flanged arcuate cradle support having a space in the flange is provided between the handle and double jaw near the pivot member, a curved leaf spring having one end affixed to one side of the handle and the other free end extending through the space in the flange of the cradle for engaging a V clamp, and a stop affixed to the other side of the handle opposite the curve of the spring.

* * * * *